United States Patent
Kopp et al.

(10) Patent No.: US 10,078,019 B2
(45) Date of Patent: Sep. 18, 2018

(54) CONFIGURABLE CHIRAL FIBER TIP-POSITIONED SENSOR

(71) Applicant: Chiral Photonics, Inc., Pine Brook, NJ (US)

(72) Inventors: Victor Il'ich Kopp, Fair Lawn, NJ (US); Jonathan Singer, New Hope, PA (US); Daniel Neugroschl, Suffern, NY (US)

(73) Assignee: Chiral Photonics, Inc., Pine Brook, NJ (US)

( * ) Notice: Subject to any disclaimer, the term of this patent is extended or adjusted under 35 U.S.C. 154(b) by 0 days.

(21) Appl. No.: 15/612,354

(22) Filed: Jun. 2, 2017

(65) Prior Publication Data

US 2017/0268937 A1    Sep. 21, 2017

Related U.S. Application Data

(63) Continuation of application No. 13/354,688, filed on Jan. 20, 2012, now abandoned.

(51) Int. Cl.
*G01K 11/32* (2006.01)
*G01N 21/21* (2006.01)

(52) U.S. Cl.
CPC .......... *G01K 11/3206* (2013.01); *G01N 21/21* (2013.01)

(58) Field of Classification Search
CPC .... G01K 11/3206; G01K 11/32; G01N 21/21; G01N 21/774; G01N 33/2823
USPC ........................................................ 356/73.1
See application file for complete search history.

(56) References Cited

U.S. PATENT DOCUMENTS

| | | |
|---|---|---|
| 6,396,859 B1 | 5/2002 | Kopp et al. |
| 6,404,789 B1 | 6/2002 | Kopp et al. |
| 6,411,635 B1 | 6/2002 | Kopp et al. |
| 6,671,293 B2 | 12/2003 | Kopp et al. |
| 6,678,297 B2 | 1/2004 | Kopp et al. |
| 6,721,469 B2 | 4/2004 | Kopp et al. |
| 6,741,631 B2 | 5/2004 | Kopp et al. |
| 6,744,943 B2 | 6/2004 | Kopp et al. |
| 6,792,169 B2 | 9/2004 | Kopp et al. |
| 6,839,486 B2 | 1/2005 | Kopp et al. |
| 6,875,276 B2 | 4/2005 | Shibayev et al. |
| 6,891,622 B2 | 5/2005 | Dyott |
| 6,891,992 B2 | 5/2005 | Kopp et al. |
| 6,925,230 B2 | 8/2005 | Kopp et al. |

(Continued)

FOREIGN PATENT DOCUMENTS

| | | |
|---|---|---|
| WO | WO 2002/073247 A2 | 9/2002 |
| WO | WO 2006/046947 A2 | 5/2006 |

(Continued)

*Primary Examiner* — Tu Nguyen
(74) *Attorney, Agent, or Firm* — Knobbe, Martens, Olson & Bear LLP

(57) ABSTRACT

The inventive configurable chiral fiber sensor with a tip-positioned sensing element, is readily configurable for use in a variety of applications (such as applications involving pressure, temperature, and even axial twist sensing), and is particularly suitable for applications requiring highly precise and accurate sensor readings within corresponding predefined limited sensing ranges. Advantageously, the inventive configurable chiral fiber sensor with a tip-positioned sensing element, is operable to utilize a wide variety of light sources, photodetectors, and related devices for sensor interrogation.

14 Claims, 1 Drawing Sheet

(56) References Cited

U.S. PATENT DOCUMENTS

| | | |
|---|---|---|
| 7,009,679 B2 | 3/2006 | Kopp et al. |
| 7,095,911 B2 | 8/2006 | Kopp et al. |
| 7,142,280 B2 | 11/2006 | Kopp et al. |
| 7,242,702 B2 | 7/2007 | Kopp et al. |
| 7,308,173 B2 | 12/2007 | Kopp et al. |
| 7,463,800 B2 | 12/2008 | Kopp et al. |
| 7,983,515 B2 | 7/2011 | Zhang et al. |
| 8,218,921 B2 | 7/2012 | Kopp et al. |
| 8,326,099 B2 | 12/2012 | Singer et al. |
| 8,457,456 B2 | 6/2013 | Kopp et al. |
| 8,463,094 B2 | 6/2013 | Kopp et al. |
| 8,712,199 B2 | 4/2014 | Kopp et al. |
| 8,948,547 B2 | 2/2015 | Kopp |
| 9,766,407 B2 | 9/2017 | Weiner et al. |
| 9,810,845 B2 | 11/2017 | Kopp |
| 9,817,191 B2 | 11/2017 | Kopp et al. |
| 9,851,510 B2 | 12/2017 | Kopp |
| 9,857,536 B2 | 1/2018 | Kopp et al. |
| 9,885,825 B2 | 2/2018 | Kopp |
| 2002/0003827 A1 | 1/2002 | Genack et al. |
| 2002/0069676 A1 | 6/2002 | Kopp et al. |
| 2002/0118710 A1 | 8/2002 | Kopp et al. |
| 2002/0172461 A1 | 11/2002 | Singer et al. |
| 2003/0118285 A1 | 6/2003 | Kopp et al. |
| 2004/0145704 A1 | 7/2004 | Kopp et al. |
| 2008/0098772 A1 | 5/2008 | Kopp et al. |
| 2009/0289617 A1* | 11/2009 | Bohnert ................. 324/96 |
| 2009/0324159 A1 | 12/2009 | Kopp et al. |
| 2010/0002983 A1 | 1/2010 | Kopp et al. |
| 2010/0158438 A1 | 6/2010 | Churikov et al. |
| 2011/0292676 A1 | 12/2011 | Weiner et al. |
| 2011/0293219 A1 | 12/2011 | Weiner et al. |
| 2012/0189241 A1 | 7/2012 | Kopp et al. |
| 2012/0257857 A1 | 10/2012 | Kopp et al. |
| 2013/0121641 A1 | 5/2013 | Singer et al. |
| 2013/0188174 A1 | 7/2013 | Kopp et al. |
| 2013/0188175 A1 | 7/2013 | Kopp et al. |
| 2013/0216184 A1 | 8/2013 | Kopp et al. |
| 2015/0212274 A1 | 7/2015 | Kopp |
| 2017/0219774 A1 | 8/2017 | Kopp |
| 2017/0269277 A1 | 9/2017 | Weiner et al. |
| 2017/0269293 A1 | 9/2017 | Churikov et al. |
| 2017/0276867 A1 | 9/2017 | Kopp |
| 2017/0336570 A1 | 11/2017 | Kopp et al. |
| 2017/0336659 A1 | 11/2017 | Kopp et al. |

FOREIGN PATENT DOCUMENTS

| | | |
|---|---|---|
| WO | WO 2008/080174 A1 | 7/2008 |
| WO | WO 2017/053479 A1 | 3/2017 |
| WO | WO 2017/100667 A1 | 6/2017 |

* cited by examiner

CONFIGURABLE CHIRAL FIBER TIP-POSITIONED SENSOR

The present patent application is a continuation of U.S. application Ser. No. 13/354,688, entitled "CONFIGURABLE CHIRAL FIBER TIP-POSITIONED SENSOR," filed Jan. 20, 2012.

FIELD OF THE INVENTION

The present invention relates generally to optical fiber-based sensors, and more particularly to a highly sensitive chiral fiber sensor with a tip-positioned sensing element that is readily configurable for use in a variety of applications requiring highly precise, sensitive, and/or accurate sensor readings within corresponding predefined limited sensing range, and that may be interrogated utilizing only light sources and photodetectors.

BACKGROUND OF THE INVENTION

Fiber-based sensors have many important applications in a wider range of industries. However, such sensing systems often suffer from a number of common disadvantages, such as complexity of interrogation systems, and vulnerability of the fiber sensing elements and the links between the sensing elements and the interrogating systems to events and stimuli that are not intended to be sensed but that may nevertheless impact the sensor system performance, accuracy and reliability.

A co-pending commonly assigned U.S. patent application entitled "CONFIGURABLE CHIRAL FIBER SENSOR", which is hereby incorporated herein in its entirety, advantageously discloses various embodiments of a novel configurable chiral fiber sensor solution that are readily configurable for use in a variety of applications (such as applications involving pressure and/or temperature sensing), and that are particularly suitable for applications in which the sensing of a presence, or an absence, of a target sensed event (e.g., specific minimum pressure or minimum temperature) is required. Advantageously, the novel configurable chiral fiber sensor utilized light sources, photodetectors, and related devices for sensor interrogation.

However, there are certain practical applications which require very precise and accurate sensor readings, and/or readings that are very sensitive in the sensed parameter variations, and in which the scope of a total range of sensed parameter values is of lesser or limited importance. It would thus be desirable to provide a configurable chiral fiber sensor with the advantages of the sensor disclosed in the above-incorporated patent application, but that would be operable to satisfy the high precision/responsiveness/sensitivity requirements.

SUMMARY OF THE INVENTION

Figure 1:
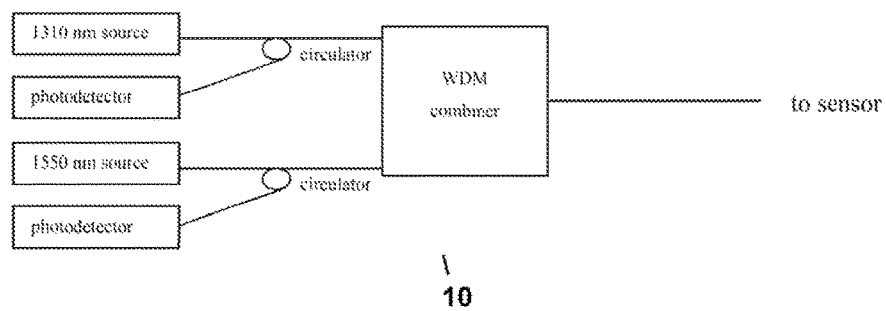
FIG. 1 is a schematic diagram of a side view of a first exemplary embodiment of the configurable chiral fiber tip-positioned sensor of the present invention.

The novel inventive chiral fiber sensor with a tip-positioned sensing element, is readily configurable for use in a variety of applications (such as applications involving pressure, temperature, and even axial twist sensing), and is particularly suitable for applications requiring highly precise and accurate sensor readings within corresponding predefined limited sensing ranges.

Advantageously, the inventive configurable chiral fiber sensor with a tip-positioned sensing element, is operable to utilize a wide variety of light sources, photodetectors, and related devices for sensor interrogation.

In at least one exemplary embodiment thereof, the inventive chiral fiber sensor with a tip-positioned sensing element comprises at least one predefined compatible light source operable to generate a light signal having a predefined range of polarization characteristic parameters, an optical fiber link of a predetermined length, having a first end connected to the at least one predefined compatible light source, and a second end, an optical fiber sensing component, positioned at the second end of the optical fiber link, operable to permit the light signal to be received from the at least one light source, and to be circulated therethrough, at least one transducer means, positioned proximal to the optical fiber sensing component, for causing, in response to at least one sensable event, at least one corresponding proportional distortion, in the predefined polarization characteristics of the circulating light signal, and within the predefined parameter range thereof, and a sensor interrogation system, operable to detect the at least one proportional distortion to produce a corresponding at least one proportional sensor output.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claim(s).

DETAILED DESCRIPTION OF THE INVENTION

The system and method of the present invention advantageously overcome and address the drawbacks of previously known fiber-based sensors and provide additional beneficial features.

The inventive configurable chiral fiber sensor, in various embodiments thereof, is readily configurable for use in a variety of applications (such as applications involving pressure, temperature, and even' axial twist sensing), and is particularly suitable for applications which require very precise and accurate sensor readings, and/or readings that are very sensitive in the sensed parameter variations, and in which the scope of a total range of sensed parameter values is of lesser or limited importance.

In one embodiment thereof, the inventive chiral fiber sensor comprises a modified optical fiber sensing portion comprising a tip-mounted sensing element operable to reflect polarized light and, when unstressed, to maintain the polarization of light signals passing therethrough), where at least a portion of the light signals being circulated through the novel sensor system comprise linearly polarized light components that are sensitive to changes in the physical characteristics of the sensing element (for example, caused by changes in element ambient temperature, application of even slight pressure thereto, and/or application of a twisting force thereto—all without the need for a proximal transducer, which of course may still be used if desired).

The sensing component responds to the sensed changes in the sensing element by proportionally changing the orientation of the linearly polarized light signal components passing therethrough. The light signals and various polarized components thereof are preferably generated and circulated by use of appropriately interconnected light sources, circulators, photodetectors, and a WDM combiner).

Referring now to FIG. 1, an exemplary embodiment of the inventive configurable chiral fiber sensor is shown as a chiral fiber sensor 10. In at least one exemplary embodiment thereof, the chiral fiber sensor 10 comprises an optical fiber sensing component connected, through an optical fiber link of a desired length to the sensor 10's interrogation system, for example comprising at least one light source. (e.g., shown by way of example only in FIG. 1 as a pair of light sources (e.g., LEDs), one operating at a 131.0 nm wavelength (e.g., not working as a polarizer), and the other operating at a 1550 nm wavelength (e.g., working as a polarizer), each connected to a corresponding circulator which are in turn connected to a WDM combiner that communicates with the sensing component through the optical fiber link.

Figure 2:
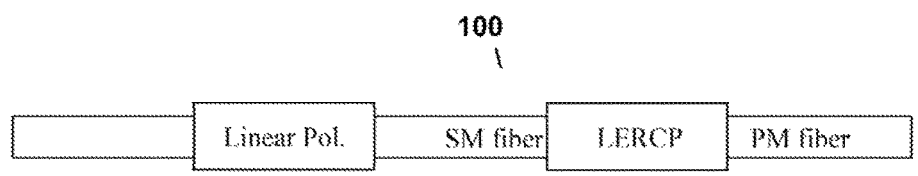
FIG. 2 is a schematic diagram of a side view of a second exemplary embodiment of the configurable chiral fiber tip-positioned sensor of the present invention.

Referring now to FIG. 2, an exemplary embodiment of the sensing component and sensing element thereof, that may be advantageously utilized as the sensing component of the chiral fiber sensor 10 of FIG. 1, is shown as a sensing component 100. The sensing component 100 includes a linear polarizer connected to a sequentially positioned single mode (SM) optical fiber section, followed by a sequentially positioned chiral fiber circular polarizer, with a polarization maintaining (PM) optical fiber sensing element (tip) positioned at its other end. Optionally, the PM sensing element may be fabricated from a microstructured PM fiber to enable utilization thereof in harsh environments (e.g., for high temperature sensing applications, etc.). The chiral fiber circular polarizer used in the sensor component 100 may be any of the circular polarizers disclosed in the co-pending commonly assigned U.S. Patent Application entitled "CHIRAL FIBER CIRCULAR POLARIZER" of Kopp et al., that is hereby incorporated by reference herein in its entirety.

It should be noted, that the limitation on the scope of the sensing range of the sensing component 100, is determined by the nature of the operation of the chiral fiber circular polarizer component thereof (shown as LERCP on FIG. 2)—its' response to alteration in the sensing element (tip) characteristics (caused by one or more sensed events), through changing of the orientation of circulated linearly polarized light components, means that the change us only clearly identifiable and attributable to the presence of the sensed event when the total caused liner polarization component rotation is between 0 and 90 degrees.

Thus, while there have been shown and described and pointed out fundamental novel features of the inventive apparatus as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

We claim:

1. A configurable optical chiral fiber sensor, comprising:
   at least one light source operable to generate a light signal having polarization characteristic parameters;
   an optical fiber link of a length, having a first end connected o said at least one light source, and a second end;
   an optical fiber sensing component, positioned at said second end of said optical fiber link, said optical fiber sensing component comprising:
   a single mode optical fiber section positioned proximal to said second end of said optical fiber link;
   a polarization maintaining optical fiber sensing element; and
   a chiral fiber circular polarizer therebetween having a single mode end connected to said single mode optical fiber section and polarization maintaining end connected to said polarization maintaining optical fiber sensing element;
   wherein said optical fiber sensing component is configured to cause a change in orientation of a linearly polarized light signal in response to at least one sensed event; and
   a sensor interrogation system, operable to detect said change in the orientation of the linearly polarized light signal to produce a corresponding at least one proportional sensor output.

2. The configurable optical chiral fiber sensor of claim 1, further comprising a linear polarizer.

3. The configurable optical chiral fiber sensor of claim 2, wherein said optical fiber sensing component comprises said linear polarizer positioned between said second end of said optical fiber link and said single mode optical fiber section.

4. The configurable optical chiral fiber sensor of claim 1, wherein said sensing element is operable to reflect at least one of linearly polarized light components into said chiral fiber circular polarizer.

5. The configurable optical chiral fiber sensor of claim 4, wherein said change in said orientation of said linearly polarized light signal comprises a change in orientation of said reflected at least one of said linearly polarized light components attributable to said at least one sensed event.

6. The configurable optical chiral fiber sensor of claim 5, further comprising a linear polarizer, wherein said sensor interrogation system comprises a circulator positioned between said light source and said linear polarizer.

7. The configurable optical chiral fiber sensor of claim 6, wherein said sensor interrogation system comprises a detector connected to said circulator such that said detector is capable to sense said change in said orientation of said linearly polarized light signal.

8. The configurable optical chiral fiber sensor of claim 1, wherein said at least one light source is operable to generate at least two different wavelengths and at least one of a plurality of photodetectors is operable to detect the at least two different wavelengths.

9. The configurable optical chiral fiber sensor of claim 8, wherein said at least one light source is configured to polarize light at at least one wavelength of the at least two different wavelengths and to transmit but not polarize light at at least one other wavelength of the at least two different wavelengths.

10. The configurable optical chiral fiber sensor of claim 1, wherein said configurable optical chiral fiber sensor does not comprise a transducer.

11. The configurable optical chiral fiber sensor of claim 1, wherein said polarization maintaining optical fiber sensing element comprises a polarization maintaining fiber.

12. The configurable optical chiral fiber sensor of claim 1, wherein the chiral fiber circular polarizer comprises an LER circular polarizer.

13. The configurable optical chiral fiber sensor of claim 1, wherein the configurable optical chiral fiber sensor is sensitive to changes in temperature.

14. The configurable optical chiral fiber sensor of claim 1, wherein the configurable optical chiral fiber sensor is sensitive to changes in pressure.

* * * * *